(12) United States Patent
Bosies et al.

(10) Patent No.: US 6,689,616 B1
(45) Date of Patent: Feb. 10, 2004

(54) DYE-POLYSACCHARIDE CONJUGATES AND THEIR USE AS A DIAGNOSTIC AGENT

(75) Inventors: Elmar Bosies, Weinheim (DE); Heinz-Michael Hein, Seeheim-Jugenheim (DE); Rudolf Reiter, Weilheim (DE); Hans Peter Josel, Weilheim (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/581,650

(22) PCT Filed: Dec. 17, 1998

(86) PCT No.: PCT/EP98/08282

§ 371 (c)(1),
(2), (4) Date: Jan. 12, 2001

(87) PCT Pub. No.: WO99/31183

PCT Pub. Date: Jun. 24, 1999

(30) Foreign Application Priority Data

Dec. 17, 1997 (EP) .............................................. 97122248

(51) Int. Cl.$^7$ ......................... G01N 33/00; G01N 30/02; G01N 21/76

(52) U.S. Cl. .......................... 436/70; 436/161; 436/164; 436/172

(58) Field of Search .......................... 436/70, 164, 161, 436/172

(56) References Cited

U.S. PATENT DOCUMENTS 6,280,703 B1 * 8/2001 Combs et al. ............. 424/1.11

* cited by examiner

*Primary Examiner*—Jill Warden
*Assistant Examiner*—Monique T. Cole
(74) *Attorney, Agent, or Firm*—Barnes & Thornburg

(57) ABSTRACT

New dye-polysaccharide and dye-cyclosaccharide conjugates and their use as a diagnostic agent especially for determining the glomerular filtration rate in humans.

6 Claims, No Drawings

DYE-POLYSACCHARIDE CONJUGATES AND THEIR USE AS A DIAGNOSTIC AGENT

The present invention concerns new dye-polysaccharide conjugates and their use as a diagnostic agent especially for determining the glomerular filtration rate in humans.

The glomerular filtration rate is very important for diagnostic and therapeutic measures in pre-clinical and clinical situations since it allows the determination of renal functional impairment. The glomerular filtration rate (GFR) is understood as the amount of primary urine produced by the glomeruli of the kidneys per unit of time which can be determined with any substance that is only filtered and is neither secreted by the tubules nor re-absorbed from the primary urine.

The clearance of the test substance used is examined in order to quantify the glomerular filtration rate. Clearance refers to the amount of plasma in ml which is cleared of a particular (test) substance by the kidneys in a unit of time (min).

At present various methods are used to determine this clearance. Thus endogenous creatinine clearance, inulin clearance and $^{51}$Cr-EDTA ($Na_2$$^{51}$Cr-ethylenediamine tetraacetate) clearance have become important. X-ray contrast media such as iohexol are also used to determine the renal clearance.

However, all the listed methods have serious disadvantages. Hence depending on the respective procedure for determining clearance it is necessary to continuously infuse the test substance to maintain a constant plasma level and/or to collect urine by an unpleasant catheterisation and/or to take several blood samples. Determination of the inulin concentration in the plasma or urine is a complicated method and has a relatively large margin of error. The use of radioactively labelled substances is an additional burden for the organism and should therefore be avoided if possible.

The so-called input clearance is regarded as the most elegant way of determining clearance. In this case the excretion of a marker is not measured directly but rather the plasma concentration of the marker is kept constant. The required amount of marker which is necessary to keep the plasma concentration constant corresponds to the amount of marker excreted by the kidneys and thus to the clearance. This of course requires continuous monitoring of the plasma concentration which nowadays can only be accomplished with the aid of radioactively labelled substances.

A considerable improvement would be to use non-radioactively labelled markers whose plasma concentration could be continuously monitored. In addition blood withdrawal and urine collection would not be required to determine the concentration of the marker.

The object was therefore to find a non-radioactively labelled marker which is completely eliminated by renal ultrafiltration i.e. it is neither secreted nor re-absorbed by the tubuli and whose plasma concentration can be determined continuously by an invasive or non-invasive method, the non-invasive method being preferred and whose plasma concentration is determined in particular by transcutaneous absorption measurements.

The present invention solves this problem by using polysaccharides which are covalently linked to a dye such that the plasma concentration of the whole molecule can be determined transcutaneously by absorption measurement with the aid of a detector.

Such compounds have already been described in the literature. Thus there are conjugates of the dye Cibacron Blue with amylose, glucans and cellulose (Anal. Biochem. 31, 412 (1969); Acta Chem. Scand. 25, 298 (1971)); Biochem. J. 87, 90 (1963), the so-called blue dextran (Anal. Biochem. 39, 202 (1971) and the dye Remazole Brilliant Blue R linked to amylose (Experientia 23, 805 (1967)). In all these dye-polysaccharide conjugates the polysaccharide is a polysaccharide composed of glucose units. However, these are relatively rapidly metabolically degraded and are therefore unsuitable for determining the renal clearance. On the other hand such polysaccharides are not eliminated solely by glomerular filtration through the kidney and are therefore also not suitable for this reason for determining the renal clearance.

Polysaccharides that are preferably used within the sense of the present invention are polyfructosans such as inulin, levan, asparagosine, sinistrin, fibrulin, graminin, phlein, poan, secalin and irisin which are eliminated from the kidney by glomerular filtration. These are substances with chain lengths of 10–30 fructose units some of which carry a glucose molecule at the end of the chain. Polysaccharides of the inulin type or of the more water-soluble sinistrin are preferably used.

Dyes are used as the dye components of the conjugates which carry a functional group such as a carboxyl, hydroxylsulfonyl, amino, isothiocyanato or isocyanato group. These functional residues can be directly reacted with a polysaccharide or be bound to the polysaccharide by means of a spacer.

The dye components of the conjugates used according to the invention have an absorption maximum in the range between 500 and 1300 nm, preferably between 600 and 900 nm. Phthalocyanine, phenazine, phenothiazine, phenoxazine, rhodamine, azo, triphenylmethane and cyanine dyes and derivatives thereof are particularly suitable for this. Representative dyes are for example triphenylmethanes, indocyanines, oxazines and rhodamines.

Hence the invention concerns compounds of the general formula I $$F—X(spacer)_n-Y—E—(CH_2)_m—PS \qquad (I)$$

in which
F is a dye component with an absorption maximum between 500 and 1300 nm, preferably between 600 and 900 nm,
n=0 or 1,
m=0 or 1,
if n=0, X=—CO, —NH—C=O, —NH—C=S, —NH—C=NH, —CONH—C=S
if n=1, X=NH, —CONH, —SO$_2$NH, —NHCONH, —NHCSNH,
spacer=a $C_2$–$C_6$ alkylene group which is optionally substituted by a hydroxy group or the group

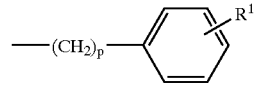

in which p=0–4 and $R_1$ hydrogen or can be a sulfonic acid group,
Y=a valence dash, —CH$_2$, —NHCOCH$_2$, —NH—C=O, —NH—C=S, —NH—C=NH,
E=O or NH
and PS=a polyfructosan and if E=O and m=0, the oxygen atom via which the polysaccharide is bound is part of this polysaccharide, and if E=NH it is an aminated or aminoalkylated polyfructosan.

Preferred compounds in the sense of the invention are above all those in which X=—CO, —NH, —CONH, —SO$_2$NH, —NH—C=O, —NH—C=S, spacer=a C$_2$–C$_6$ alkylene group or a group

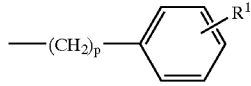

in which p is preferably 0 or 1 and R$_1$ represents hydrogen, n=0 or 1,

Y=valence dash, —CH$_2$, —NH—COCH$_2$, —NH—C=O, m=0 or 1,

E=O or NH and PS preferably represents a sinistrin or inulin residue or an aminated or aminoalkylated derivative of sinistrin or inulin.

In particular compounds of the general formula I are emphasized in which F represents a triphenylmethane, indocyanine, oxazine or rhodamine dye, X represents a —CO—, —CONH— group, spacer represents a C$_2$–C$_4$ residue, n=0 or 1, m=0 or 1, Y=valence dash, CH$_2$ or —NHCOCH$_2$ and E=O or NH and the polysaccharide is sinistrin, inulin or an aminated or aminoalkylated derivative of sinistrin or inulin.

The polysaccharides can have reacted once or several times with the dyes and thus have different degrees of occupancy.

In order to improve water-solubility, the compounds of the general formula I can optionally be subsequently derivatized on the polysaccharide unit. Derivatives with 2-hydroxypropyl or carboxymethyl groups on the polysaccharide unit are especially suitable for this. Compounds of the general formula I can also be reacted with sulfones such as 1,4-butanesulfone to improve water-solubility and also to neutralize excess amino groups. These substances are also a subject matter of this invention.

Substances of the general formula I can be prepared by generally known processes, preferably by 1. reacting a dye derivative of the general formula II

F—Z (II)

in which
    F represents a dye component with an absorption maximum of 500–1300 nm,
    Z represents an —NCO, —NCS, —NC=NH, —CONCS or the group G-spacer-NCO, G-spacer-NCS, G-spacer-NCNH, in which G=NH, —CONH, —SO$_2$NH, —NH—CO—NH, —NH—CS—NH and spacer has the above-mentioned meanings,
    with a polyfructosan of the general formula III

HO—PS (III)

in which PS—OH represents one of the polyfructosans listed above or 2. reacting a dye derivative of the general formula IV

F—D (IV), in which D represents an NH$_2$ or a G-spacer-NH$_2$ group in which F, G and spacer have the above-mentioned meanings, with a polyfructosan derivative of the general formula V

in which PS has the above-mentioned meaning or 3. reacting a dye derivative of the general formula IV

F—D (IV)

in which F and D have the above-mentioned meanings, with a polyfructosan derivative of the general formula VI

PS—O—CH$_2$—COOH (VI)

in which PS has the above-mentioned meaning or 4. reacting a dye derivative of the general formula VII

F—A (VII)

in which F has the above-mentioned meaning and A denotes an active ester group such as N-hydroxysuccinimide ester or N-hydroxybenzotriazole ester, an acyl chloride or sulfonyl chloride group, with an amine of the general formula VIIIa or VIIIb H$_2$N-spacer-Y—O—PS (VIIIa)

H$_2$N—(CH$_2$)$_m$—PS (VIIIb)

in which spacer and PS have the above-mentioned meanings, Y=valence dash, —CH$_2$, —NHCOCH$_2$, —NH—C=O, —NH—C=S, —NH—C=NH, m=0 or 1.

An isocyanate derivative of the general formula II is prepared in situ by thermal decomposition of the corresponding carboxylic acid azide as described in Chem. Pharm. Bull. 33, 1164 (1985). A dye-isocyanate derivative of the general formula II is reacted with a polysaccharide of the general formula III for example analogously to Makromol. Chemie, 121, 18 (1968).

Isothiocyanates of the general formula II can be prepared from amines of the general formula F—NH$_2$, in which F has the above-mentioned meaning, analogously to Chem. Ber. 63, 888 (1930), J. Chem. Soc. 125, 1702 (1924) or Chem. Ber. 86, 314 (1953). They are reacted with polysaccharides of the general formula III analogously to Chem. Zentralblatt 1910, 910 or Am. Chem. J. 22, 464 or J. Am. Chem. Soc. 65, 900 (1943).

Amines of the general formula IV in which D represents a G-spacer-NH$_2$ group are known in the literature or are prepared by known methods. Thus for example if G=CONH or SO$_2$NH, a carboxylic acid or sulfonic acid of the general formula F—CO$_2$H or F—SO$_3$H in which F has the above-mentioned meaning is reacted via the corresponding active ester (reaction scheme see below) or the corresponding acid chloride is reacted with a diamine of the general formula H$_2$N-spacer-NH$_2$ in which spacer has the above-mentioned meaning under suitable reaction conditions to form an amide of the general formula IV (for this see J. Med. Chem. 27, 1481 (1984), J. Prakt. Chem. 130, 293 (1931), J. Med. Chem. 34, 73 (1991) and Liebigs Ann. Chem. 1988, 787).

Polysaccharide derivatives of the general formula V are prepared by reacting the polysaccharide with cyanogen bromide. Such compounds are described for example in Nature 214, 1302 (1967) or Eur. J. Biochem. 18, 351 (1971). The subsequent reaction with amine derivatives of the general formula IV to form compounds of the general formula I is described among others in Carbohydrate Res. 20, 1 (1971). Polyfructosan-acetic acids of the general formula VI are described among others in Methods Carbohydr. Chem. 6, 384 (1972) and Khim. Prir. Soedin 1969, 525.

Polyfructosan-carboxylic acid derivatives of the general formula VI are reacted in an activated form with amines of the general formula IV. In this case active esters are particularly suitable as the active form. Thus a carboxylic acid of the general formula VI is reacted with alcohols such as N-hydroxysuccinimide or N-hydroxy-benzotriazole in the presence of a dehydrating agent such as dicyclohexylcarbodiimide in inert solvents such as ethyl acetate, dichloromethane, tetrahydrofuran or N,N-dimethylformamide. The active ester prepared in this manner is usually used directly in the subsequent reaction with addition of organic bases such as triethylamine. However, the reaction can also be carried out very well in water which in some cases is preferred for solubility reasons. In this case N-ethyl-N'(3-trimethylammonio-propyl)carbodiimide iodide is preferably used as the carbodiimide. However, the reaction can also be carried out using N-ethyl-N'(3-dimethylaminopropyl)carbodiimide without the addition of for example N-hydroxysuccinimide.

A dye derivative of the general formula VII is reacted with amines of the general formulae VIIIa and VIIIb analogously to the process described in the previous paragraph or analogously to p. 10. Some of the compounds of the general formula VIIIa are described in the literature (Starch 48 (5), 191 (1996); J. Nucl. Med. 27, 513 (1986)). However, they can also be prepared by reacting a polyfructosan-acetic acid of the general formula VI with a mono-protected alkylene-diamine analogously to the process described in the previous paragraph. In this case a carbobenzoxy group is particularly suitable as a protective group which can subsequently be readily cleaved off catalytically with hydrogen.

Amines of the general formula VIIIa can also be prepared by deprotonating the polyfructosan with sodium hydride in an inert solvent such as N,N-dimethylformamide, subsequently alkylating it with e.g. p-cyanobenzyl bromide and hydrogenating the nitrile obtained in this manner in the presence of Raney nickel or Raney cobalt with addition of concentrated ammonia in a methanol-water mixture. The alkylation can for example also be carried out with 2-bromoethylamine to obtain an O-amino-ethyl-polysaccharide (J. Nucl. Chem. 27, 513 (1986)). Amines of the general formula VIIIb can be prepared in the following manner. Reaction of a polyfructosan with p-toluenesulfochloride in an inert solvent such as e.g. N,N-dimethylformamide in the presence of a base yields a p-toluenesulfonate of the polyfructosan and the degree of occupancy depends on the amount of p-toluene sulfochloride used. Reaction of this sulfonic acid ester with sodium azide in a solvent such as N,N-dimethyl-formamide at temperatures of 80–100° C. produces the corresponding azide from which a polyfructosan is formed by catalytic reduction with hydrogen which carries an amino group directly on the hydrocarbon backbone. If this sulfonic acid ester is reacted with sodium cyanide in for example N,N-dimethylformamide at temperatures between 80–1000 Celsius, the corresponding nitrile is obtained which can be reduced by catalytic hydrogenation with Raney nickel or Raney cobalt in a methanol-water mixture in the presence of concentrated ammonia to form the desired primary amine. In this case the hydrocarbon backbone carries an aminomethyl group.

Other processes for preparing aminated or aminoalkylated polysaccharides are described in the literature (s. e.g. J. Med. Chem. 31, 898 (1988)). Hence one or several hydroxyl groups in a polysaccharide can be oxidized under suitable reaction conditions with sodium periodate to form the aldehyde which is then reduced with cyanoborohydride in the presence of an amine to form the alkylated amine. In this case monoprotected alkylene diamines are preferably used as the amine component and a carbobenzoxy group is preferably used as the protective group. This protective group can then be catalytically dehydrogenated under generally known conditions in water as the solvent.

Compounds of the general formula I can be subsequently converted into more water-soluble substances by reaction with chloroacetic acid or propene oxide analogously to processes known in the literature. Thus the reaction of a polysaccharide with chloroacetic acid is described among others in Methods Carbohydr. Chem. 6, 384 (1972) or Makromol. Chem. 122, 272 (1969) and the reaction of a polysaccharide with propene oxide is described in Starch Chemistry and Technology, Academic Press New York (1984), R. L. Whistler et al.

The compounds according to the invention of the general formula I are usually administered intravenously. For this 10–25% isotonic, aqueous solutions are used which contain the usual additives for injections such as stabilizers and buffers. Sodium or potassium phosphate buffer are preferably used as buffers, antioxidants can optionally be used as stabilizers. In order to obtain an isotonic solution, sodium chloride or mannitol is added. The pH of the solution is between 6.5 and 8, preferably between pH=7 and 7.5. The compounds according to the invention of the general formula I are administered singly in an amount of 0.1–5 g, preferably 0.2–2 g.

The following examples show some process variants which can be used to synthesize the compounds according to the invention. However, they are not intended to represent a limitation of the subject matter of the invention. The structure of the compounds was established by $^1$H and $^{13}$C nuclear resonance spectroscopy. In addition the conjugates that were prepared were checked by gel permeation chromatography (Ultrahydrogel™ 250, 7.8×300 mm column from the Waters Company; flow: 0.5 ml/min; water). In this case the $\lambda_{max}$ values for the polysaccharide and dye components were determined at the same time t.

Dyes Used for the Coupling

JA 243

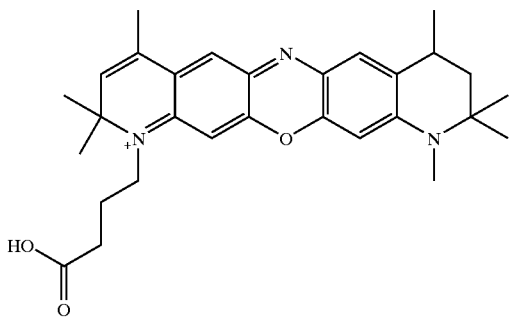

(described in EP 0 543 333 A1)

JA 133-OSU

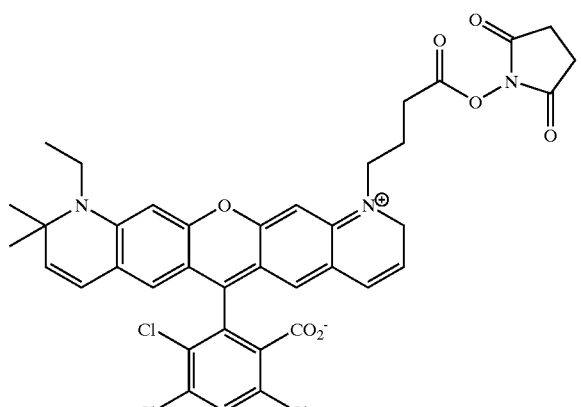

(described in EP 0 567 622 B1)

1

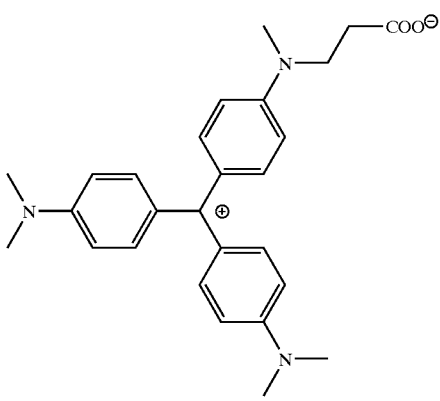

Synthesis of 1

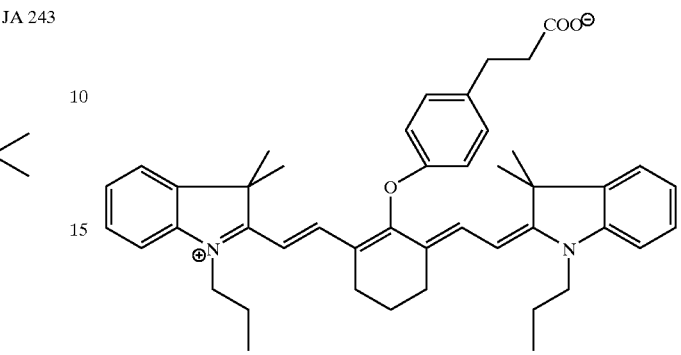

a) ethyl acrylate, glacial acetic acid
b) Michler's ketone, POCl$_3$
N-(2-ethoxycarbonyl-ethyl)-N-methyl-aniline. based on the procedure in: *Organikum*, 1988, 17th edition, 334.

1. 25.9 g N-(2-ethoxycarbonyl-ethyl)-N-methyl-aniline (125 mmol) was heated with 6.71 g (25 mmol) Michler's ketone and 9.20 g phosphoroxychloride (60 mmol) for 3 hours in a water bath. The mixture was stirred overnight at room temperature, 500 ml water was added and it was alkalinized with caustic soda (400 mmol in 100 ml water). Then 100 ml distillate was initially distilled off with steam. After adding 10 g caustic soda in 50 ml water, an additional 150 ml was removed by distillation in a stream of water vapour. The brown precipitate was suction filtered, rewashed with water, stirred for 20 minutes at 90° C. with 300 ml 1 N hydrochloric acid and hot filtered. The crude product was salted out, recrystallized from water (precipitates firstly as an oil) and dried in a vacuum over calcium chloride.

Yield: 8.55 g (73%) metallic green solid.

1-Hydroxysuccinimide ester: 1.0 g 1 (1.72 mmol, calculated for 1×HCl) was dissolved at 0° C. in 25 ml dry acetonitrile, and 375 mg (2.5 mmol) N-hydroxy-succinimide and 670 mg (2.6 mmol) dicyclohexyl-carbodiimide were added. The cooling bath was removed after 30 minutes and the mixture was stirred for 2.5 hours at room temperature. The solution obtained in this manner was filtered and processed further in a crude form.

Synthesis of 2

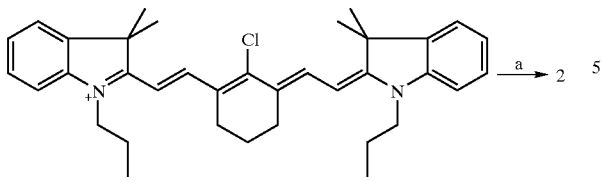

IR 780 Iodide (Aldrich)

a) 3-(4-hydroxyphenyl)-propionic acid, NaH, DMF 2. 573 mg (3.45 mmol) 3-(4-hydroxyphenyl)-propionic acid was added at 0° C. to 6.9 mmol sodium hydride in 50 ml dimethylformamide. The heterogeneous mixture was stirred for 30 minutes at room temperature, subsequently 2.00 g (3.00 mmol) solid Aldrich IR 780 iodide was added and it was stirred overnight at room temperature. The whole reaction mixture was applied to a column packed with silica gel/chloroform and chromatographed with a mobile solvent gradient of chloroform to chloroform:methanol=70:30.

Yield: 1.45 g (61%) deep green solid with a metallic lustre.

2-hydroxysuccinimide ester: 413 mg (3.59 mmol) N-hydroxysuccinimide was added to 1.60 g (2.39 mmol) 2 in 50 ml dry acetonitrile and cooled in an ice bath to 0° C. 741 mg (3.59 mmol) dicyclohexylcarbodiimide was added and the mixture was stirred overnight in a melting ice bath. The reaction mixture was filtered, the solvent was removed and the residue was dried in a vacuum.

Yield: 1.43 g crude product, processed further without purification.

EXAMPLE 1

Conjugate of 1 with O-Aminoethylinulin 1.00 g O-aminoethylinulin ($M_r$ ca. $175_n$, 5.71 mmol; content of free amino groups ca. 0.57 mmol) was dissolved in 20 ml water and a solution of 1-hydroxy-succinimide ester (10 ml, 0.69 mol) in acetonitrile (content based on the non-activated acid=69 μmol/ml) was added within 3 minutes. 5 ml 1-hydroxysuccinimide solution (0.35 mmol) was added after 3 hours and again after 5 hours and the mixture was stirred for 2 days at room temperature. The solvent was removed by distillation under reduced pressure, the residue was dried in a vacuum and taken up in 150 ml methanol. The crude product precipitated after adding 150 ml acetone. It was centrifuged, slurried twice in acetone and again centrifuged. For the purification it was taken up in a small amount of water, filtered and chromatographed in two portions over a gel column (BioRad Bio-Gel, P-2 fine, column 2.5×60 cm, flow ca. 1 ml/min eluant:distilled water).

Yield: 630 mg, deep violet solid; $\lambda_{max}$ at 204 and 590 nm after 12 minutes.

Aminoethylation of Inulin
A Reaction with Bromoethylamine

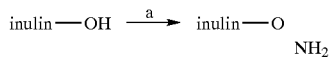

a) Br(CH$_2$)$_2$NH$_2$HBr, NaOMe, DMSO

Lit.: J. G. McAfee, F. D. Thomas, G. Subramanian, R. D. Schneider, B. Lyons, M. Roskopf, C. Zapf-Longo, D. Whaley, *J.Nucl. Chem.* 1986, 27, 513–520.

B Synthesis via N-Carbobenzoxy-bromoethylamine

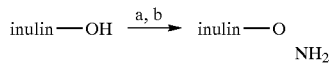

a) Br(CH$_2$)$_2$NHZ, NaH, DMF b) H$_2$/Pd—C, H$_2$O, MeOH

O-(aminoethyl)inulin. Inulin (2.00 g, 12.3 mmol with reference to the fructose units) was dissolved at ca. 30° C. in dry dimethylformamide (30 ml) and sodium hydride (2.22 g, wetted with ca. 40% oil, 55.5 mmol) was added at room temperature. N-carbobenzoxy-2-bromoethylamine (4.76 g, 18.4 mmol) was added after 30 minutes and heated to 100° C. An additional 4.76 g N-carbobenzoxy-2-bromoethylamine was added within 15 minutes and the reaction mixture was stirred for 2.5 hours at 100° C. and overnight at room temperature. While cooling in an ice bath, an equal volume of water was carefully added and ammonium chloride solution (1.07 g in 5 ml water) was added. The solvent was removed by distillation at a reduced pressure, the residue was dried in a vacuum and taken up in 200 ml water. It was shaken out with diethyl ether and the aqueous phase was concentrated to ca. 5 ml (a precipitate which may occur is removed by filtration).

It was purified by means of preparative gel permeation chromatography. BioRad Bio-Gel, P-2 fine. Column 2.5×60 cm, flow ca. 1 ml/min eluant:distilled water.

Yield: 1.70 g.

Cleavage of the Carbobenzoxy Protective Group:

150 mg N-carbobenzoxy-aminoethylinulin was taken up in 10 ml water, 1 ml methanol and 75 mg palladium-carbon (Chempur, 10% Pd on C) were added and it was hydrogenated under normal pressure for 2 days at room temperature. The catalyst was removed by filtration, the solvent was removed from the filtrate and the residue was dried in a vacuum.

Yield: 111 mg.

EXAMPLE 2

Conjugate of JA 243 and O-Aminoethylinulin 20 mg O-aminoethylinulin ($M_r$ ca. $175_n$, 110 μmol) was dissolved in 0.5 ml water and heated to 50° C. For this purpose two portions of a solution of 10 mg JA 243-hydroxysuccinimide ester (17.5 μmol; described in EP 0 543 333 A1) in 1 ml acetonitrile were added dropwise at an interval of one hour. An additional 3 mg of solid dye-active ester (5.2 μmol) was added after 4 hours and the mixture was stirred at room temperature for 20 hours. The solvent was removed by distillation at a reduced pressure and the residue was dried in a vacuum. Purification was by gel permeation chromatography (BioRad Bio-Gel, P-2 extra fine, column 1×20 cm, eluant:distilled water)

Yield: 13 mg deep blue solid; $\lambda_{max}$ at 204 and 660 nm after 12.5 minutes.

EXAMPLE 3

Conjugate of JA 133 and O-Aminoethylinulin 750 mg O-aminoethylinulin ($M_r$ ca. $175_n$, 4.3 mmol) was dissolved in 7 ml water. 4 ml acetonitrile was added dropwise. The clear solution was heated to 40° C. and 210 mg (0.25 mmol) solid JA 133-OSu was added. 100 μl N-methylmorpholine and 2 ml acetonitrile were added after 2 hours. The mixture was stirred for 20 hours at room temperature during which an additional 130 mg (0.15 mmol) JA 133-OSu was added after 3 hours. 100 mg (0.12 mmol) JA 133-OSu was again added after 5 hours at 45° C. and it was stirred overnight at room temperature. Water was added for the processing and it was shaken out four times with chloroform. The aqueous solution was kept for 3 hours at 35° C., concentrated and chromatographed on a gel column (BioRad Bio-Gel, P-2 extra fine, column 2.5×35 cm, flow ca. 0.2 ml/min eluant:distilled water).

Yield: 415 mg; $\lambda_{max}$ at 204 and 621 nm after 16 minutes.

EXAMPLE 4

Conjugate of 2 with O-(3-Aminopropyl)inulin 1.00 g O-(3-aminopropyl)inulin (Cosun Company Industrial Inulin Derivatives) (carbonate/hydrogencarbonate mixture, occupancy: 0.60 aminopropyl groups/fructose unit) was dissolved at room temperature in 20 ml water and 12.5 ml acetonitrile was added dropwise. Firstly 1.14 g and after 1 hour an additional 0.1 g 2-hydroxy-succinimide ester was added to this solution. The reaction mixture was stirred overnight, 200 ml water was added and it was shaken out three times with chloroform. The product was pre-purified on a gel column (BioRad Bio-Gel, P-2 extra fine, column 2.5×20 cm, eluant: distilled water) and subsequently chromatographed (same conditions, column 2.5×40 cm)

Yield: 600 mg.

EXAMPLE 5

Conjugate of JA 133 and O-(3-Aminopropyl)inulin 700 mg O-(3-aminopropyl)inulin was dissolved in 14 ml water at room temperature and acetonitrile was added dropwise until a turbidity persisted. 0.5 ml water was added and the solution which was now clear was admixed with 690 mg (0.821 mmol) solid JA 133-OSU. The mixture was stirred overnight at room temperature, 200 ml water was added and it was shaken out three times with chloroform. The aqueous phase was rotary evaporated, taken up in a small amount of water and chromatographed on a gel column (BioRad Bio-Gel, P-2 extra fine, column 2.5×35 cm, eluant:distilled water).

Yield: 550 mg.

EXAMPLE 6

Conjugate of JA 133 with 3a

8 µl N-ethylmorpholine was added to 4.4 mg 3a in 90 µl water and 30 µl acetonitrile. A solution of 4 mg JA 133-OSu in 80 µl acetonitrile and 240 µl water was added to this. 3 mg JA 133-OSU in 60 µl acetonitrile and 180 µl water was added after 6 days at an interval of 2.5 hours. After 1 further day the solvent was removed, it was taken up in 1 ml water and chromatographed over a gel column (BioRad Bio-Gel, P-2 extra fine, column 2×13 cm, eluant:distilled water).

Yield 1.5 mg; $\lambda_{max}$ at 204 and 621 nm.

Synthesis of 3a

Carboxymethylinulin. Lit.: D. L. Verraest, J. A. Peters, J. G. Batelaan, H. v. Bekkum, Carbohydrate Research, 1995, 271, 101–112.

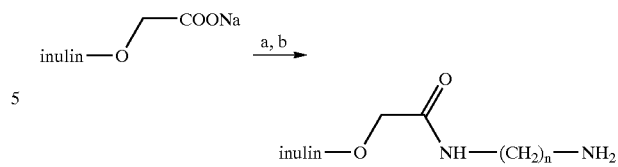

3a: n=2
3b: n=3 a) $H_2N(CH_2)_nNHZ$, 1-ethyl-3-(3-dimethyl-aminopropyl) carbodiimide×HCl
b) $H_2/Pd$—C, $H_2O$ n=2. 1.91 g (8.67 mmol) carboxymethylinulin was dissolved in 19 ml 2-morpholinoethane sulfonic acid-sodium hydroxide buffer (pH 4.75). 3.32 g (17.3 mmol) 1-ethyl-3-(3-dimethylaminopropyl)carbodiimide hydrochloride and 2.00 g (8.67 mmol) N-carbobenzoxy-diaminoethane hydrochloride (FLUKA) were added at room temperature. After 1 hour it was briefly heated to 40° C. and stirred overnight at room temperature. A further 2.39 g (12.4 mmol) 1-ethyl-3-(3-dimethylaminopropyl)-carbodiimide hydrochloride was added and it was stirred for a further 5 hours. The solution was adjusted to pH 11 with sodium hydroxide solution, the precipitate was separated, the aqueous phase was shaken out three times with 80 ml dichloromethane and dialysed against aqueous sodium chloride solution (containing toluene).

Yield: 870 mg.

Cleavage of the Protective Group:

300 mg of the N-carbobenzoxy-protected aminoinulin derivative was dissolved in 5 ml water, 50 mg catalyst (10% palladium on C) was added and it was hydrogenated for 5 hours at 40 mbar. The solution was filtered and lyophilized.

Yield: 143 mg.

EXAMPLE 7

Conjugate of JA 243 with 3a

11 µl N-ethylmorpholine was added to 6 mg 3a in 250 µl water and 250 µl acetonitrile. 3.7 mg and after 3 hours 2.7 mg JA 243-hydroxysuccinimide ester (described in EP 0 543 333 A1) each in 50 µl acetonitrile and 50 µl water were added dropwise to the solution that was now clear. 8.2 µl N-ethylmorpholine was added and it was stirred overnight. After removing the solvent, it was possible to isolate the product by preparative gel permeation chromatography (BioRad Bio-Gel, P-2 extra fine, column 2×30 cm, eluant-:distilled water).

Yield: 1.8 mg; $\lambda_{max}$ at 204 and 660 nm.

EXAMPLE 8

Conjugate of 1 with 3a

A solution of 600 mg 3a in 25 ml water was admixed with 1 ml N-ethylmorpholine and a solution of 2.15 mmol 1-hydroxysuccinimide ester in 25 ml acetonitrile was added. The mixture was stirred overnight and a further 2.15 mol 1-hydroxysuccinimide ester in 25 ml acetonitrile was added. After 5 hours 100 ml water was added, it was heated to 50° C. and allowed to stand overnight at room temperature. The solvent was removed, the residue was stirred out with 100 ml methanol and centrifuged. The supernatant was discarded, the crude product was taken up in 20 ml water and purified by preparative gel permeation chromatography (conditions see example 7).

Yield: 420 mg; $\lambda_{max}$ at 204 and 590 nm.

EXAMPLE 9

Conjugate of JA 133 with 3b 30 mg 3b was dissolved in a mixture of 0.3 ml water and 0.2 ml acetonitrile, and 38 µl N-ethylmorpholine was added. The solution obtained in this manner was added dropwise at room temperature to 5 mg (6 µmol) JA 133-OSu in 60 µl water and 40 µl acetonitrile. After 2.5 hours the reaction mixture was added dropwise to a further 5 mg (6 µmol) JA 133-OSu in 60 µl water and 40 µl acetonitrile and it was stirred overnight. The solvent was removed and the residue was dried in a vacuum. It was taken up in 0.2 ml water and purified by gel chromatography (BioRad Bio-Gel, P-2 extra fine, column 2×30 cm, eluant:distilled water).

Yield: 25 mg; $\lambda_{max}$ at 204 and 621 nm.

Synthesis of 3b 208 mg (0.95 mmol) carboxymethylinulin was dissolved in 2 ml 0.2 M 2-morpholinoethane sulfonic acid-sodium hydroxide buffer (pH 4.75) and admixed with 362 mg (1.89 mmol) 1-ethyl-3-(3-dimethylaminopropyl)carbodiimide hydrochloride. The pH was adjusted to 4.75 with hydrochloric acid, 231 mg (0.95 mmol) N-carbobenzoxy-diaminoethane hydrochloride (FLUKA) was added and the mixture was stirred overnight at room temperature. The pH was again adjusted to 4.75 with sodium hydroxide solution and neutralized after a further 4 hours. The product solution was extracted with dichloromethane and dialysed for 2 days against water.

Yield: 126 mg.

Cleavage of the Protective Group:

Procedure as with n=2. 46 mg free amine was obtained from 102 mg N-carbobenzoxy-amine. The compounds described above and further preferred compounds are listed in the following table.

| Example No | F | X | spacer | n | Y | E | m | Ps |
|---|---|---|---|---|---|---|---|---|
| 1 | 1 | —CONH— | —CH$_2$—CH$_2$— | 1 | — | O | Ø | inulin |
| 2 | JA 243 | —CONH— | —CH$_2$—CH$_2$— | 1 | — | O | Ø | inulin |
| 3 | JA 133 | —CONH— | —CH$_2$—CH$_2$— | 1 | — | O | Ø | inulin |
| A | JA 243 | —CONH— | —CH$_2$—CH$_2$— | 1 | — | O | Ø | sinistrin |
| 4 | 2 | —CONH— | —CH$_2$—CH$_2$— | 1 | —CH$_2$— | O | Ø | inulin |
| 5 | JA 133 | —CONH— | —CH$_2$—CH$_2$— | 1 | —CH$_2$— | O | Ø | inulin |
| B | JA 243 | —CONH— | —CH$_2$—CH$_2$— | 1 | —CH$_2$— | O | Ø | sinistrin |
| 6 | JA 133 | —CONH— | —CH$_2$—CH$_2$— | 1 | —NH—CO—CH$_2$— | O | Ø | inulin |
| 7 | JA 243 | —CONH— | —CH$_2$—CH$_2$— | 1 | —NH—CO—CH$_2$— | O | Ø | inulin |
| 8 | 1 | —CONH— | —CH$_2$—CH$_2$— | 1 | —NH—CO—CH$_2$— | O | Ø | inulin |
| C | JA 133 | —CONH— | —CH$_2$—CH$_2$— | 1 | —NH—CO—CH$_2$— | O | Ø | sinistrin |
| 9 | JA 133 | —CONH— | —CH$_2$—CH$_2$—CH$_2$— | 1 | —NH—CO—CH$_2$— | O | Ø | inulin |
| D | JA 243 | —CONH— | —CH$_2$—CH$_2$—CH$_2$— | 1 | —NH—CO—CH$_2$— | O | Ø | sinistrin |
| E | JA 133 | —CONH— | —CH$_2$—CH$_2$—CH$_2$—CH$_2$— | 1 | —NH—CO—CH$_2$ | O | Ø | inulin |
| F | 2 | —CONH— | —CH$_2$—CH$_2$—CH$_2$— | 1 | —NH—CO—CH$_2$ | O | Ø | inulin |
| G | 2 | —CONH— | —CH$_2$—CH$_2$—CH$_2$—CH$_2$— | 1 | —NH—CO—CH$_2$ | O | Ø | inulin |
| H | 2 | —CO— | — | Ø | — | NH | Ø | inulin |
| I | 2 | —CO— | — | Ø | — | NH | 1 | inulin |
| K | JA 133 | —CO— | — | Ø | — | NH | 1 | inulin |
| L | JA 133 | —CO— | — | Ø | — | NH | 1 | inulin | m and n = Ø denotes "zero"
Y and spacer = — denotes: valence dash
The carboxyl group of the residue X is identical to the carboxyl group of the corresponding dye F.

What is claimed is:

1. Compounds of formula I $$F—X-(spacer)_n-Y—E—(CH_2)_m—PS \qquad (I),$$

in which

F is a dye component with an absorption maximum between about 500 and about 1300 nm, n=0 or 1, m=0 or 1, if n=0, X —CO, —NH—C=O, —NH—C=S, —NH—C=NH, —CONH—C=S, if n=1, X=NH, —CONH, —SO$_2$NH, —NHCONH, —NHCSNH, spacer=a C$_2$–C$_6$ alkylene group or the group

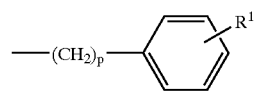

in which p=0–4 and R$_1$ hydrogen or can be a sulfonic acid group,

Y=a valence dash, —CH$_2$, —NHCOCH$_2$, —NH—C=O, —NH—C=S, —NH—C=NH,

E=O or NH and PS=a polyfructosan and if E=O and m=0, the oxygen atom via which the polysaccharide is bound is part of this polysaccharide, and if E=NH it is an aminated or aminoalkylated polyfructosan.

2. Compounds of formula I as claimed in claim 1, in which X=—CO, —NH, —CONH, —SO$_2$NH, —NH—C=O, —NH—C=S, spacer=a $C_2$–$C_6$ alkylene group or a group

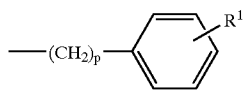

in which
p is optionally 0 or 1 and $R_1$ represents hydrogen,
n=0 or 1,
Y=valence dash, —$CH_2$, —NH—$COCH_2$, —NH—C=O,
m=0 or 1,
E=O or NH and PS optionally represents a sinistrin or inulin residue, or an aminated or aminoalkylated derivative of sinistrin or inulin.

3. A diagnostic agent comprising a compound as claimed in claim 1.

4. A method for determining the glomerular filtration rate using a dye as claimed in claim 1, wherein the concentration of the dye is determined at intervals or continuously.

5. The method of claim 4, wherein the determination is not carried out invasively.

6. The compounds of claim 1 wherein F is a dye component with an absorption maximum between about 600 and about 900 nm.

* * * * *